United States Patent
Brånemark et al.

(10) Patent No.: US 8,377,106 B2
(45) Date of Patent: Feb. 19, 2013

(54) IMPLANT AND AN IMPLANT MEMBER

(75) Inventors: Rickard Brånemark, Mölndal (SE); Peter Thomsen, Frölunda (SE)

(73) Assignees: Rickard Branemark Consulting AB, Mölndal (SE); Biomaterial Development Goteborg AB, Västra Frölunda (SE)

(*) Notice: Subject to any disclaimer, the term of this patent is extended or adjusted under 35 U.S.C. 154(b) by 1441 days.

(21) Appl. No.: 11/792,914

(22) PCT Filed: Dec. 12, 2005

(86) PCT No.: PCT/SE2005/001895
§ 371 (c)(1),
(2), (4) Date: Dec. 14, 2007

(87) PCT Pub. No.: WO2006/065205
PCT Pub. Date: Jun. 22, 2006

(65) Prior Publication Data
US 2008/0125868 A1    May 29, 2008

(30) Foreign Application Priority Data
Dec. 13, 2004 (SE) .................... 0403020

(51) Int. Cl.
*A61B 17/84* (2006.01)
(52) U.S. Cl. .................... 606/300
(58) Field of Classification Search ........ 606/60, 606/300, 301, 310, 319, 321, 331, 76
See application file for complete search history.

(56) References Cited

U.S. PATENT DOCUMENTS

| | | | | |
|---|---|---|---|---|
| 5,727,943 A * | 3/1998 | Beaty et al. | | 433/174 |
| 5,989,027 A | 11/1999 | Wagner et al. | | |
| 6,196,842 B1 * | 3/2001 | Jorneus | | 433/174 |
| 6,758,672 B2 * | 7/2004 | Porter et al. | | 433/173 |
| 6,896,517 B1 * | 5/2005 | Bjorn et al. | | 433/174 |
| 2004/0006346 A1 * | 1/2004 | Holmen et al. | | 606/73 |

FOREIGN PATENT DOCUMENTS

| | | |
|---|---|---|
| CN | 1446530 | 10/2003 |
| EP | 1 199 049 | 4/2002 |
| JP | 63-279835 A | 11/1988 |

(Continued)

OTHER PUBLICATIONS

Brånemark, Rickard, "A Biomechanical Study of Osseointegration In-vivo Measurements in Rat, Rabbit, Dog and Man," Göteborg, Sweden, 1996.

(Continued)

*Primary Examiner* — Kevin T Truong
*Assistant Examiner* — Michael Araj
(74) *Attorney, Agent, or Firm* — Drinker Biddle & Reath LLP (57) ABSTRACT

An implant and an implant member for attaching to living biological tissue of a human being or an animal. The implant has an outer surface comprising a first part and a second part which have different properties with regard to the biocompatibility of each part with biological tissue. The implant includes at least one surface portion comprising a ground surface making up the first part and one or several delimited regions making up said second part. A method for producing the implant, where a perforated masking unit is applied onto the implant, and a masking unit for the method.

10 Claims, 7 Drawing Sheets

FOREIGN PATENT DOCUMENTS

| | | |
|---|---|---|
| JP | 02-241461 A | 9/1990 |
| JP | 03-292948 A | 12/1991 |
| JP | 4-231042 | 8/1992 |
| JP | 6-304186 | 11/1994 |
| JP | 7-328036 | 12/1995 |
| JP | 9-234209 | 9/1997 |
| JP | 2001-259017 | 9/2001 |
| RU | 2 187 281 | 8/2002 |
| RU | 2 202 981 | 4/2003 |
| RU | 59 967 | 1/2007 |
| WO | 01/05325 | 1/2001 |

OTHER PUBLICATIONS

Wennerberg, Ann, "On Surface Roughness and Implant Incorporation," Dept. of Biomaterials/Handicap Research, Institute for Surgical Sciences and Dept. of Prosthetic Dentistry, Göteborg University, Sweden, 1996, p. 52.

* cited by examiner

IMPLANT AND AN IMPLANT MEMBER

This application is a National Stage Application of PCT/SE2005/001895 filed Dec. 12, 2005 which claims priority to SE Application No. 0403020-1 filed Dec. 13, 2004.

TECHNICAL FIELD

The present invention relates to and implant comprising means for attachment to living biological tissue of a human being or an animal, the implant having an outer surface comprising a first part and a second part which have different properties with regard to the biocompatibility of each part with biological tissue, to a method for producing such an implant, and to a masking unit used in said method. Further, the present invention relates to an implant member comprising means for attachment to living biological tissue of a human being or an animal, the implant having an outer surface, and to a method for producing the same.

BACKGROUND OF THE INVENTION

For a long time, different kinds of implants produced from various materials have been used in the treatment of patients, for fixation of fractures, as a substitute for removed bone tissue, in dental surgery for fixation of a denture or dental bridge, and in other applications, for example. In the end of the 19$^{th}$ century, experiments with different kinds of implant materials, such as gold, porcelain, and silver were performed. In the 1930s, the use of the metal alloy vitallium was suggested, which is a biocompatible material on which a lot of research has been conducted since then, and which is still used today. The advantageous biocompatibility of titanium was discovered by accident in the 1950s, when a titanium implant was found to be able to integrate with bone tissue. This formed the basis of the concept of osseointegration. Since then, titanium, due to its good biocompatibility, has been used for implants, in pure form or in the form of alloys. With time, titanium and titanium alloys showed superior long term results, inter alia, titanium was found to be non-carcinogenic, which results are well documented. However, in the beginning, the use of titanium and titanium alloys in implants was limited to bone tissue of good quality due to their relative bioinert properties, i.e., inability to interact with biological systems, in contrast to more bioactive materials which better can interact with biological systems, such as surrounding tissue.

There are substantially two procedures to modify the surface in order to enhance the ability of the implant to interact with the surrounding tissue. One of these is a topographical modification of the implant, for example by patterning or raising/texturing the surface to improve the contact between the implant and the tissue, and the other one is a chemical modification of the surface of the implant, but also a combination of these two procedures is possible.

Today, for the chemical modification of the surface, there are several known suitable bioactive materials which have the ability to interact with biological systems and which, for example, can be applied to the outer surface of the implant by different deposition techniques, such as plasma-spraying, pulsed-laser deposition, sputtering, blast-coating etc. Examples of such bioactive materials are, for example, calcium phosphates, such as hydroxyapatite and tricalcium phosphate.

However, there are drawbacks associated with the use of new materials and substances, as their long-term effects are unknown.

There is a need to tailor the interaction of an implant with biological tissue. It is previously known to produce implants of two different materials, where the first material covers one part of the surface of the implant and a second material covers the other part of the surface of the implant. Hereby, it is possible, to a certain degree, to adapt an implant to different requirements. However, this solution is not flexible enough and does not provide implants which are adaptable enough.

Further, there is a need to tailor the interaction of an implant with biological tissue such that an implant with a surface having bioactive properties is provided, which thereby interacts with the surrounding tissue, and at the same time has well documented long-term effects.

THE OBJECT OF THE INVENTION

The object of the present invention is therefore to provide an implant having improved surface properties and a good biocompatibility, inter alia, an implant with bioactive properties, which at the same time has well documented long-term effects. Further, the object of the present inventions is to provide a method for producing such an implant.

SUMMARY OF THE INVENTION

The above mentioned objects are achieved by providing an implant comprising means for attachment to living biological tissue of a human being or an animal, the implant having an outer surface comprising a first part and a second part which have different properties with regard to the biocompatibility of each part with biological tissue. The implant comprises at least one surface portion comprising a ground surface making up said first part and one or several delimited regions making up said second part. A method for producing the implant and a masking unit arranged to be used in the method for producing the implant are provided, where the method and the masking unit comprises the special measures and features, respectively, of first placing a perforated masking unit on the implant, and applying, from the outside of the masking unit, said one or several delimited regions in the form of deposits such that the apertures of the masking unit define said second part of the surface. Another method for producing the implant and a masking unit arranged to be used in the method for producing the implant are provided, where the method and the masking unit comprises the special measures and features, respectively, of first coating the implant with a coating, and thereafter placing a perforated masking unit onto the implant, and removing said coating from the areas of the apertures of the masking unit, whereby said one or several delimited regions are provided.

By providing a surface portion which comprises a ground surface and one or several deliberately distributed delimited regions, where the properties of the ground surface with regard to its biocompatibility with biological tissue is different from that of said one or several delimited regions, a heterogeneous structure of the surface is provided which provides the possibility to tailor the interaction of an implant with different specific biological systems, which is not possible to achieve with a homogenous structure of the surface where the outer surface of the implant comprises large areas with the same properties with regard to the biocompatibility, for example large areas of the same material. Said surface portion can be provided at specific positions on the implant where it is desirable to have a certain interaction with a specific region of the biological system after the implantation. The ground surface can be of the same material as the remaining outer surface of the implant, i.e., the outer surface outside said surface portion, or the delimited regions can be of the same material as the remaining outer surface of the implant.

According to an advantageous embodiment of the implant according to the present invention, the different properties are different with regard to the range effect in relation to said biological tissue and/or with regard to the time aspect of the interaction of each part with the biological tissue.

According to a further advantageous embodiment of the implant according to the present invention, said one or several delimited regions consist of a large number of delimited areas, the number of which exceeds five. The number of said delimited areas can advantageously exceed twenty, and in some cases exceed fifty. Said delimited areas can each have a size of 0.1 to 0.3 mm², and have a distance of at least 1 to 3 mm, advantageously at least 2 mm, to the most adjacent other delimited area. By this distribution of areas having first properties with regard to the biocompatibility with biological tissue, surrounded by the ground surface with other properties with regard to the biocompatibility with biological tissue, an implant can be given a specific biocompatibility in specific regions which facilitates the integration of said implant in the tissue.

According to another advantageous embodiment of the implant according to the present invention, said one or several delimited regions form delimited areas which are substantially circular, oval and/or strip-shaped or intermediate shapes of said shapes.

According to yet another advantageous embodiment of the implant according to the present invention, said one or several delimited regions consist of deposits, or coatings, applied to the ground surface, which deposits can have a thickness of 0.05 to 5 μm, preferably 0.1 to 3 μm. Advantageously, these deposits have a heterogeneous thickness and they are thinning out towards their boundary regions. The heterogeneous thickness and the uneven surface of the deposits promote the contact between the implant and the tissue.

According to an advantageous embodiment of the implant according to the present invention, the ground surface covers 50 to 98% of the surface portion of the implant, in some cases 70 to 95% thereof, and in other cases even 85 to 95% thereof.

According to a further advantageous embodiment of the implant according to the present invention, the outer surface of the implant comprises at least two different materials, said ground surface consisting of a first material, and said one or several delimited regions consisting of at least one second material. This embodiment enables, inter alia, the production of a biocompatible implant with bioactive properties which at the same time has well documented long-term effects, where said first material is, for example, titanium, titanium oxide, and/or a titanium alloy, which have known and well documented long-term effects, and said at least one second material comprises one or several bioactive materials which in a bioactive manner interacts with the surrounding biological tissue, or vice versa.

Examples of other materials which can be used instead of titanium are, for example, the elements niobium, hafnium, zirconium, tantalum, and various alloys or oxides of said elements, and other alloys such as stainless steel, cobalt-chrome etc.

Examples of bioactive materials are a salt of the chemical group of the periodic table, which comprises calcium, for example a material comprising calcium phosphate, or more precisely a material which comprises hydroxyapatite, polymers, macromolecules, amino acids, peptides, proteins, pharmacological drugs, cells, and other bioactive ceramics of crystalline and/or amorphous state. These can be resorbable or non-resorbable. Hydroxyapatite has been found to be particularly advantageous for dental implants.

According to an advantageous embodiment of the implant according to the present invention, both the first material and the at least one second material consist of a material which comprises one or several of the above-mentioned bioactive materials.

According to a further advantageous embodiment of the implant according to the present invention, the surface of said at least one surface portion is topographically modified, for example, by patterning or raising/texturing. Topographical modification of the surface is advantageously achieved, for example, by machining, microfabrication, blasting, cryo-blasting, etching, polishing, abrasion, or by various laser techniques.

According to another advantageous embodiment of the implant according to the present invention, the attachment means is provided with at least one thread, but also other means of attachment are possible. An alternative to threads is, for example, to provide the attachment means with a rough surface which by means of pressure is attached to the bone tissue, e.g., or with longitudinal grooves etc.

Further, the above-mentioned objects are achieved by providing an implant member comprising means for attachment to living biological tissue of a human being or an animal, the implant having an outer surface where said outer surface comprises at least one surface region, the surface of which is topographically modified, for example by patterning or raising/texturing, and by providing a method for producing the implant member, which method comprises the special measure of patterning said surface region by means of laser.

According to an advantageous embodiment of the implant member according to the present invention, the surface region is patterned by providing several recesses, and the surface region is positioned in the region of the attachment means.

According to another advantageous embodiment of the implant member according to the present invention, the attachment means is provided with at least one thread, and the surface region is positioned in the root/valley of said at least one thread, and said recesses are provided after each other along the longitudinal extension of the root.

According to other advantageous embodiments of the implant member according to the present invention, the surface region, through said recesses, has a wave shape in a cross-section plane of the attachment means, and the surface region extends at least one turn of the thread, or one pitch.

According to an advantageous embodiment of the implant member according to the present invention, the surface region has a surface with an $S_a$ between 0.8 and 10 μm, preferably between 1.2 and 5 μm, where $S_a$ is calculated by the equation:

$$S_a = \frac{1}{M*N} \sum_{j=1}^{N} \sum_{i=1}^{M} |z(x_i, y_j)|.$$

$S_a$ is an accepted parameter for specifying the roughness of the surface within the technical field of implants. A complete definition of the parameter $S_a$ and the variables in the equation is disclosed, inter alia, in Ann Wennerberg's thesis "On Surface Roughness and Implant Incorporation", Dept. of Biomaterials/Handicap Research, Institute for Surgical Sciences and Dept. of Prosthetic Dentistry, Göteborg University, Sweden, 1996, ISBN 91-628-1940-2.

Rickard Brånemark's thesis "A Biomechanical Study of Osseointegration In-vivo Measurements in Rat, Rabbit, Dog and Man", Göteborg, Sweden, 1996, ISBN 91-628-2267-5, discloses that a machined surface, with a low $S_a$ has poor elastic deformation properties and instead substantially plastic deformation properties, which biomechanically can be interpreted as meaning that the surface is too smooth, on micro-level, to engage the bone further away from the interface. Further, there are studies on dental implants showing that "large" or "rough" structures of the surface, for example comprising pores having diameters of 200-400 μm, or sintering with balls having a diameter of 100-5000 μm, are problematic.

In the studies of the applicant, the specified intervals for $S_a$ of the surface regions of said embodiment of the implant member according to the present invention, have been found to be very advantageous with regard to the interaction of the implant member with biological tissue, and have been found to provide optimized biomechanics. Further, if the surface region having a surface with an $S_a$ according to the above-mentioned intervals is combined with said recesses, which gives the surface region a wave shape in a cross-section plane of the attachment means, it is possible to reach deeply in the tissue such that the amorphous zone in the interface between the tissue and the implant is passed, and at the same time, the problems arising in the presence of "rough" surface structures do not appear.

According to another advantageous embodiment of the implant member according to the present invention, the outer surface of the implant member consists of titanium and/or titanium alloys.

By combining the special features of an implant comprising means for attachment to living biological tissue of a human being or an animal, the implant having an outer surface comprising a first part and a second part which have different properties with regard to the biocompalibility of each part with biological tissue, where the implant comprises at least one surface portion comprising a ground surface making up said first part and one or several delimited regions making up said second part, and the special features of an implant member comprising means for attachment to living biological tissue of a human being or an animal, the implant having an outer surface, where said outer surface comprises at least one surface region, the surface of which is topographically modified synergy effects in the form of an outer surface which is very advantageous with regard to the biocompatibility of the implant, or the implant member, with biological tissue are provided, and the interaction is enhanced even more in the presence of threads, flanges etc. which results in mechanical/biomechanical stability by a deep engagement in the tissue.

BRIEF DESCRIPTION OF THE DRAWINGS

The present invention will now be described, for exemplary purposes, in more detail by way of embodiments and with reference to the enclosed drawings, in which.

DETAILED DESCRIPTION OF PREFERRED EMBODIMENTS

Figure 1:
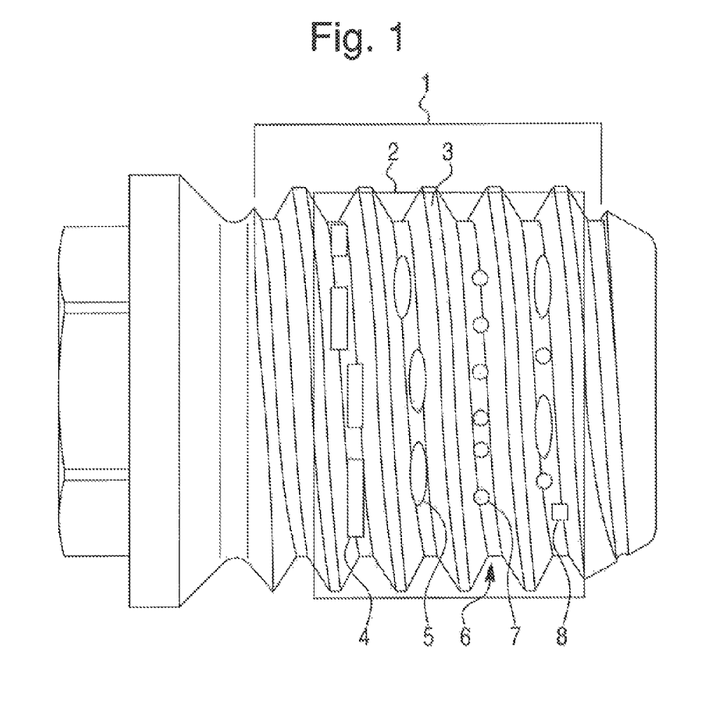
FIG. 1 is a side view of an embodiment of the implant according to the present invention, having several delimited areas in the form of deposits.
Figure 2:
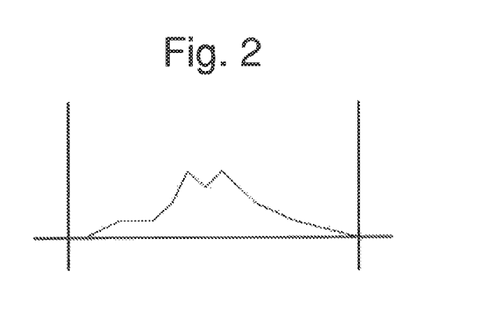
FIG. 2 is a schematic side view of the topography of a first deposit applied by an embodiment of the method according to the present invention.
Figure 3:
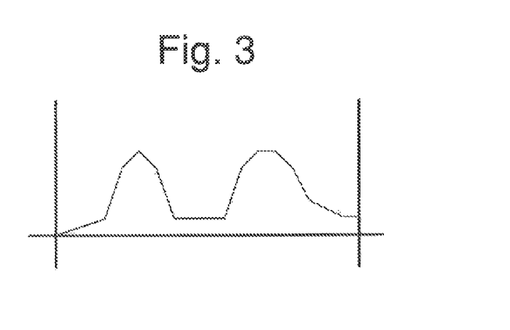
FIG. 3 is a schematic side view of the topography of a second deposit applied by an embodiment of the method according to the present invention.

FIG. 1 shows a dental implant comprising means 1 for permanent or temporary attachment to living biological tissue of a human being or an animal, which tissue can be hard or soft. The attachment means 1 comprises in this case a threaded fixation portion. The implant has an outer surface of two different materials, where the first material forms a first part of the surface and at least one second material forms a second part of the surface. The first material is titanium, but other biocompatible materials are possible, and the second material is a material comprising hydroxyapatite which is biocompatible and bioactive, but also other bioactive and/or biocompatible materials are possible. Titanium and hydroxyapatite have different properties with regard to the biocompatibility of each material with biological tissue, the different properties being different with regard to the range effect in relation to said biological tissue. The outer surface comprises a surface portion 2 which consists of a ground surface 3 of titanium, the ground surface 3 covering 70 to 90% of said surface portion 2, and of several delimited areas which consist of several deposits 4, 5, 6, 7 consisting of the material comprising hydroxyapatite, which have been applied to the root 8 of the thread of the attachment means 1, which has been found to be advantageous. The deposits 4, 5, 6, 7 have a thickness of 0.1 to 3 μm, have a heterogeneous thickness and are thinning out towards their boundary regions, which is shown in the FIGS. 2 and 3 showing the topography of a first and a second deposit, respectively, applied by an embodiment of the method according to the present invention. This results in a surface with an $S_a$ below 10 μm. The deposits 4, 5, 6, 7 cover delimited areas which are substantially circular, oval and/or strip-shaped or intermediate shapes of said shapes. The deposits 4, 5, 6, 7 can be deposited in specific regions or in special patterns to achieve the desired biological effect. The diameter of the basis of the dental implant is about 4.1 mm, and the diameter of the apex of the dental implant is about 3.75 mm. The threading is dimensioned such that there is a distance of about 0.6 mm between two crests of thread.

Figure 4:
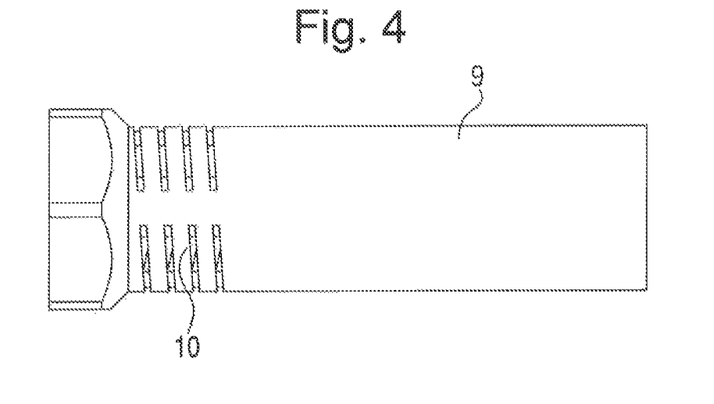
FIG. 4 is a side view of an embodiment of the masking unit according to the present invention.
Figure 7:
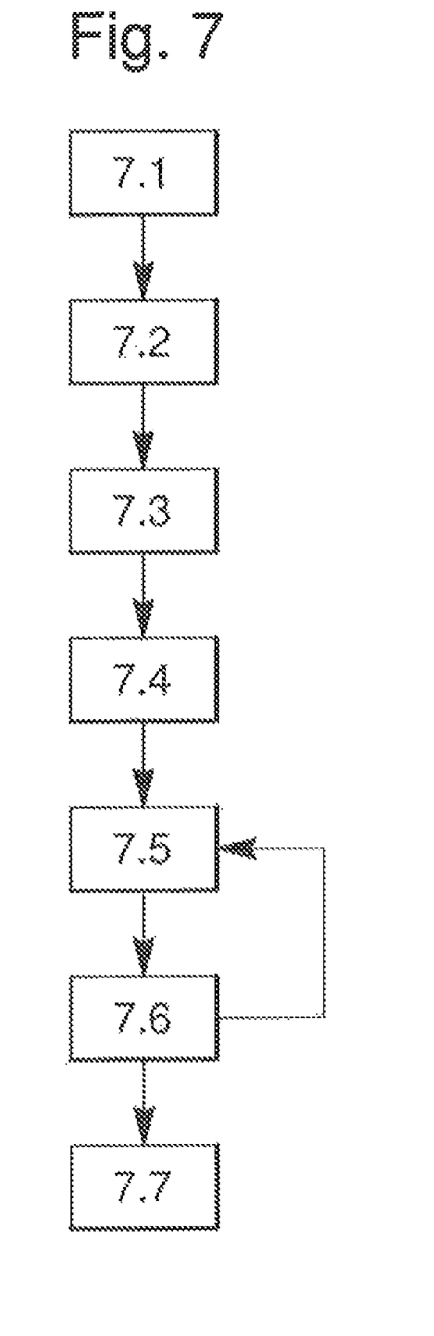
FIG. 7 is a schematic flow chart illustrating an embodiment of the method according to the present invention.

FIG. 4 shows an embodiment of the masking unit according to the present invention, which can be used in the method for producing an implant according to the invention (see FIG. 7). When applying deposits, or providing surface structures in other ways, for example by blasting, on a screw-shaped implant, a hollow cylindrical masking unit 9 is used, the inner circumference of which is adapted for the outer circumference of the implant. In particular, there should be a sufficient distance between the outer circumference of the implant and the inner circumference of the masking unit 9, such that the applied deposits are not scraped off when the masking unit 9 is removed after the process. The masking unit 9 comprises several longitudinal apertures 10, through which the material can pass and reach the implant in the method according the present invention. The masking unit 9 consists of titanium, but can also consist of titanium alloys or another suitable material.

Figure 5:
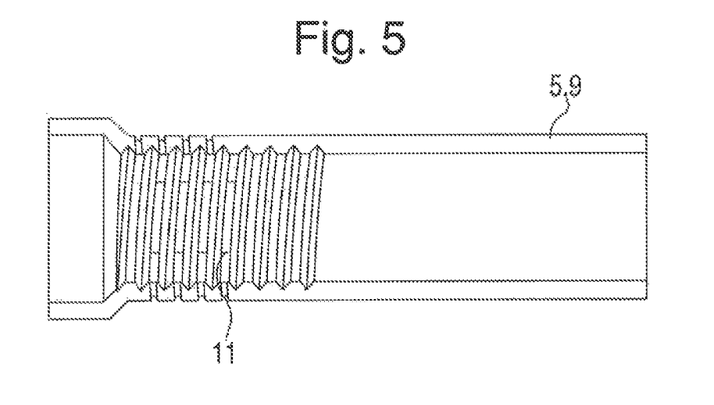
FIG. 5 is side view of an embodiment of an implant with indicated delimited areas intended to be coated with strip-shaped deposits by an embodiment of the method according to the present invention, using the masking unit of FIG. 4.

In FIG. 5 a cut away masking unit 5.9 of the masking unit of FIG. 4 is shown, thus showing the implant surrounded by the masking unit 5.9 and with indicated delimited areas 11 above which the apertures 10 shown in FIG. 4 are positioned when the implant is inserted in the masking unit 5.9.

Figure 6:
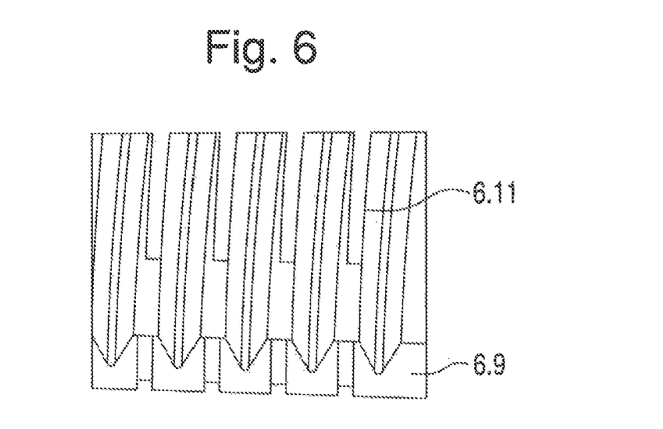
FIG. 6 is an enlargement of the indicated delimited areas of FIG. 5.

FIG. 6 shows an enlargement of said indicated delimited areas 6.11.

FIG. 7 shows a schematic flow chart illustrating an embodiment of the method according to the present invention, in which method the masking unit according to the present invention is used. Initially, the perforated masking unit is fitted onto the implant, at 7.1. The implant provided with the masking unit is inserted into a sputtering chamber, in which a target with material comprising hydroxyapatite is provided, and the chamber is pressurized with a suitable base pressure, at 7.2. A sputtering gas, in this case argon, together with a mixture of reactive gases are introduced into the chamber until a suitable working pressure is reached, at 7.3. A radio-frequency generator is operated at about 100 watt and at a frequency of about 13.56 MHz, and thus a high voltage with a high frequency is applied between the target and the implant provided with the masking unit, at 7.4, whereby the inert gas is ionized, and the ions knock out particles from the target. These particles are passed through apertures of the masking unit, the apertures defining the areas intended for coating, at a certain angle and are deposited in said areas of the implant, at 7.5, the areas corresponding to the shape of the apertures. This sputtering process is continued for one hour, whereby a deposit of about 0.1 µm is provided. Thereafter, the implant provided with the masking unit is turned, at 7.6, to expose the implant to sputtering at a second angle, in order to achieve desired deposits of material comprising hydroxyapatite, or any other suitable material, whereupon new particles from said target are passed through the apertures of the masking unit and are deposited in said areas of the implant, at 7.5. After a desired number of further angles, at which sputtering is performed, the coating of the implant is finished, at 7.7.

Further, a similar masking unit can be used in a method where an implant of titanium first is coated with a material comprising hydroxyapatite, and thereafter is inserted in a perforated masking unit, whereupon the material comprising hydroxyapatite is removed from the areas of the apertures of the masking unit.

The aperture pattern of the masking unit is adapted to the pattern of the deposits to be deposited on the surface portion of the implant. Naturally, there are several other possible methods for producing said surface portion on the implant according to the present invention, for example etching.

Figure 8:
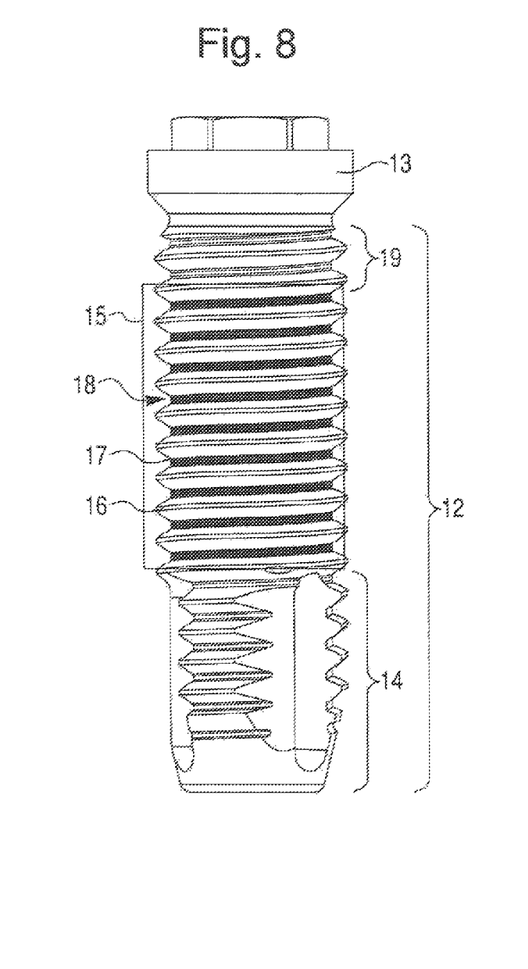
FIG. 8 is a schematic side view of an advantageous embodiment of the implant according to the present invention.

FIG. 8 shows a second dental implant comprising means 12, in the form of a threaded fixation portion, for permanent or temporary attachment to living biological tissue of a human being or an animal. The tissue can be hard or soft. Further, the implant has a basis 13 and an optionally designed apex 14. The implant has an outer surface comprising two different materials. The outer surface comprises a surface portion 15 consisting of a ground surface 16 of titanium, which covers 50 to 80% of said surface portion 15, and of several delimited areas consisting of a deposit 17 consisting of a material comprising hydroxyapatite, which has been applied to the root 18 of the thread of the attachment means 12. The deposit 17 has a helix shape which continuously winds in the root 18 of the thread, and has a thickness of 0.1 to 3 µm. However, the implant has a base portion 19 adjacent to the basis 13 where two turns of the thread do not include said deposit 17.

Figure 9:
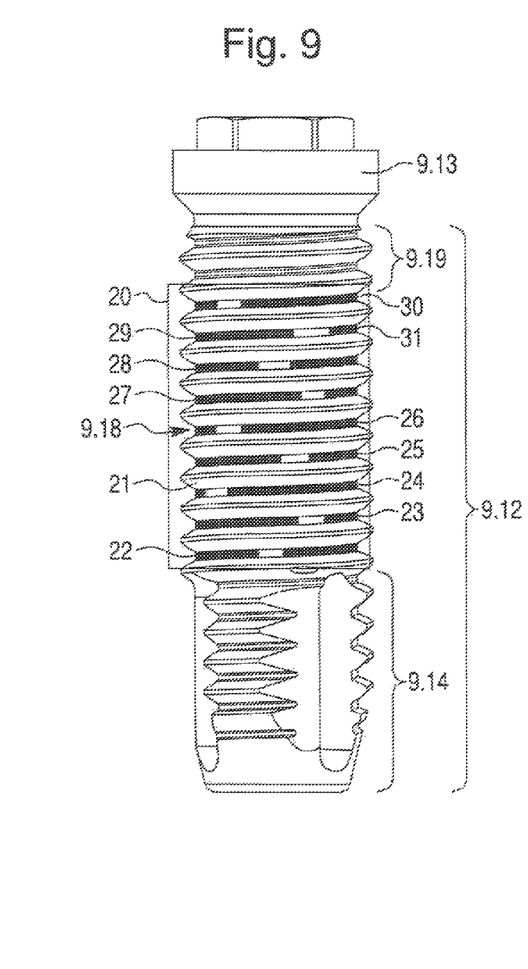
FIG. 9 is a schematic side view of a second advantageous embodiment of the implant according to the present invention.

FIG. 9 shows a third dental implant, substantially designed in the same way as the dental implant of FIG. 8, but with an outer surface having a surface portion 20 which consists of a ground surface 21 of titanium, which covers 55 to 85% of said surface portion 20, and of several delimited areas which consist of a discontinuous helix shape comprising several deposits 22, 23, 24, 25, 26, 27, 28, 29, 30, 31 consisting of a material comprising hydroxyapatite, which have been applied to the root 9.18 of the thread of the attachment means 9.12. The deposits 22, 23, 24, 25, 26, 27, 28, 29, 30, 31 are spaced apart from each other by intervals, which comprises of the ground surface 21, and extend along the root 9.18 of the thread such that the intervals between the deposits 22, 23, 24, 25, 26, 27, 28, 29, 30, 31 are irregularly positioned around the central axis of the dental implant. The deposits 22, 23, 24, 25, 26, 27, 28, 29, 30, 31 can advantageously also be distributed such that they extend along the root 9.18 of the thread in such a away that the intervals between the deposits 22, 23, 24, 25, 26, 27, 28, 29, 30, 31 are regularly positioned around the central axis of the dental implant, such that the intervals are positioned in alignment with each other along the longitudinal extension of the implant.

Figure 10:
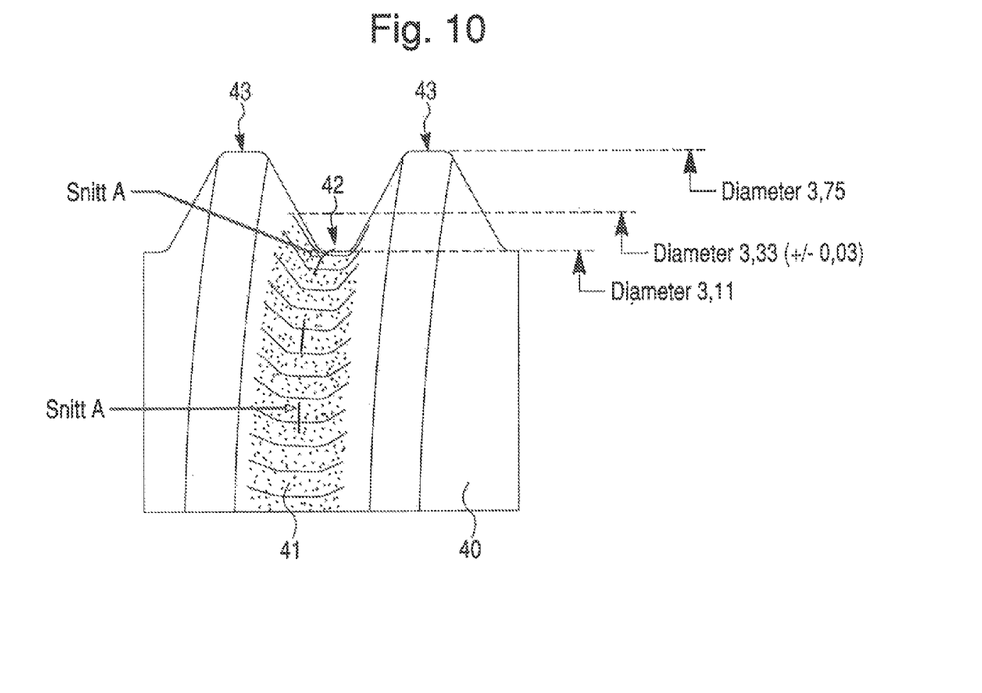
FIG. 10 is a schematic view of a portion of an embodiment of the implant member according to the present invention.

FIG. 10 shows a portion of an embodiment of the implant member according to the present invention in the form of a dental implant. More precisely, FIG. 10 shows a portion of the attachment means 40 for attachment to living biological tissue of a human being or an animal. The attachment means 40 is provided with at least one thread. The outer surface of the dental implant consists of titanium and/or titanium alloys, and said outer surface comprises at least one surface region 41, the surface of which is topographically modified by patterning, for example by means of laser. Said at least one surface region 41 is positioned in the root 42 of said at least one thread between its crests 43 of thread. The major diameter of the attachment means 40, i.e. the distance between a crest 43 of thread and a diametrically opposite crest of thread, is 3.75 mm, and the minor diameter of the attachment means 40 is 3.11 mm. The surface region is patterned by providing several recesses which are provided after each other along the longitudinal extension of the root 42. In the root 42 the recesses can be laterally displaced in relation to each other such that a slight "zigzag" structure is provided. The surface region extends along at least one turn of the thread.

Figure 11:
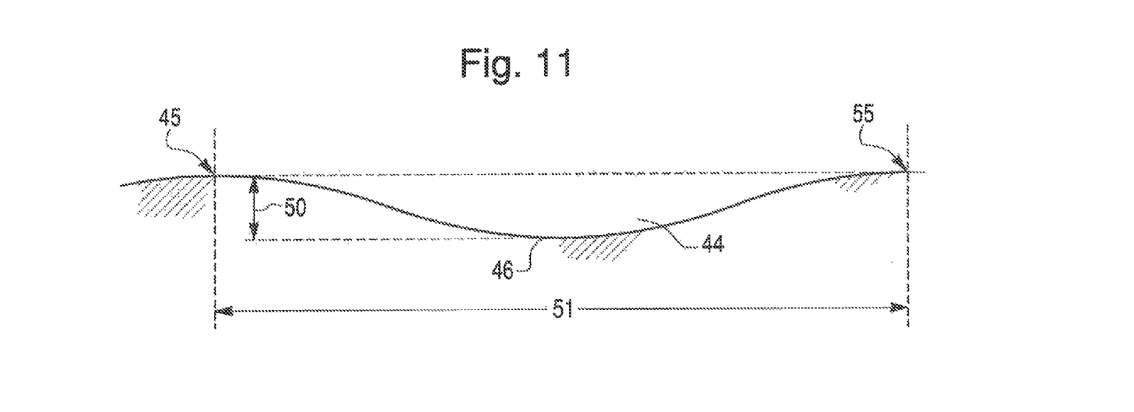
FIG. 11 shows a section along line AA of FIG. 10.

FIG. 11 shows the section AA of FIG. 10, which is not shown according to scale. The surface region has a wave shape in a cross-section plane of the attachment means, where the wave shape is substantially sinusoidal. Each crest 44, 55 of the wave raises above the valley 46 of the wave by a distance 50, the distance 50 being no more than 200 µm, advantageously not more than 150 µm, and advantageously the distance 50 is between 5 and 40 µm, which is the case in FIG. 11. The distance 51 between two adjacent crests 45, 55 of the wave is advantageously between 50 and 200 µm, more advantageously between 70 and 150 µm, and more precisely between 90 and 120 µm. However, in this embodiment the distance 51 is between 100 and 110 µm. The surface region has a surface with an $S_a$ between 1.2 and 5 µm, where $S_a$ is calculated by the equation:

$$S_a = \frac{1}{M*N}\sum_{j=1}^{N}\sum_{i=1}^{M}|z(x_i, y_j)|.$$

As previously mentioned, $S_a$ is an accepted parameter for specifying the roughness of the surface within the technical field of implants. A complete definition of $S_a$ is disclosed, inter alia, in the thesis by Ann Wennerberg mentioned in the summary. By this above-mentioned surface of the surface region it is possible to reach the fully mineralized bone tissue after bone remodelling, and therewith the desired biomechanical effect is achieved. Said surface of the surface region has a sufficiently small modification of the surface to result in little injury when the implant is inserted, but at the same time has such a rough modification of the surface that a biomechanical effect is provided. In contrast, large/rough surface structures may give, but not with total certainty, an increased mechanical effect, but with increased tissue injury as a result upon the insertion, and, additionally, a longer distance is provided into which the bone has to grow in order to reach the same effect, and this ought to result in longer healing periods for rough surfaces to heal to the tissue.

Figure 12:
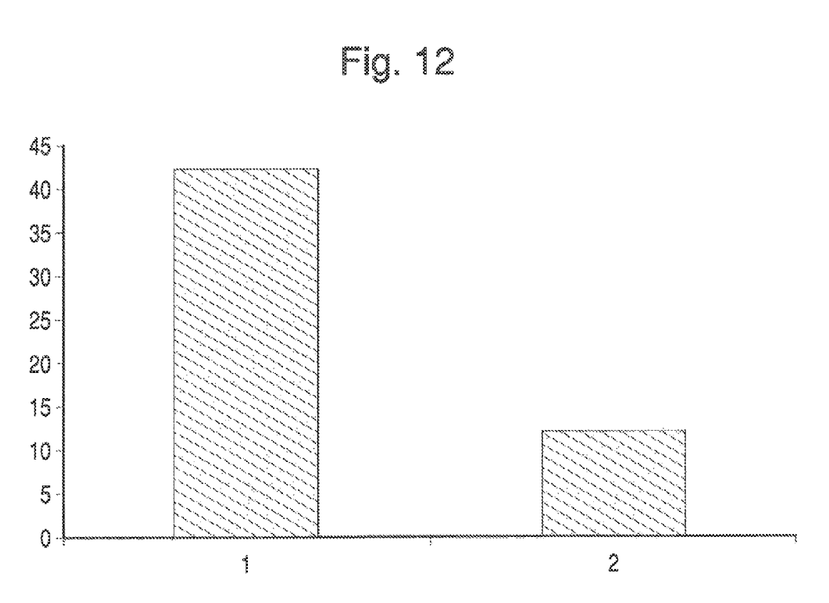
FIG. 12 is a bar chart showing the interaction between the embodiment of FIG. 10 and biological tissue.

FIG. 12 shows schematically the result of experimental studies on animals performed by the applicant. The bar "1" shows the removal torque for an implant according to the present invention, and the bar "2" shows the removal torque for an implant which is only machined in a conventional manner. Further, this study shows that, in addition to a higher removal torque according to the bar chart, a different fracture mechanics is achieved, resulting in a distinct fracture. This supports the assumption that a desired elastic deformation has resulted after removal torque of an implant according to the present invention, in contrast to previous observations of a dominating plastic deformation at the interface of implants machined in a conventional manner.

Figure 13:
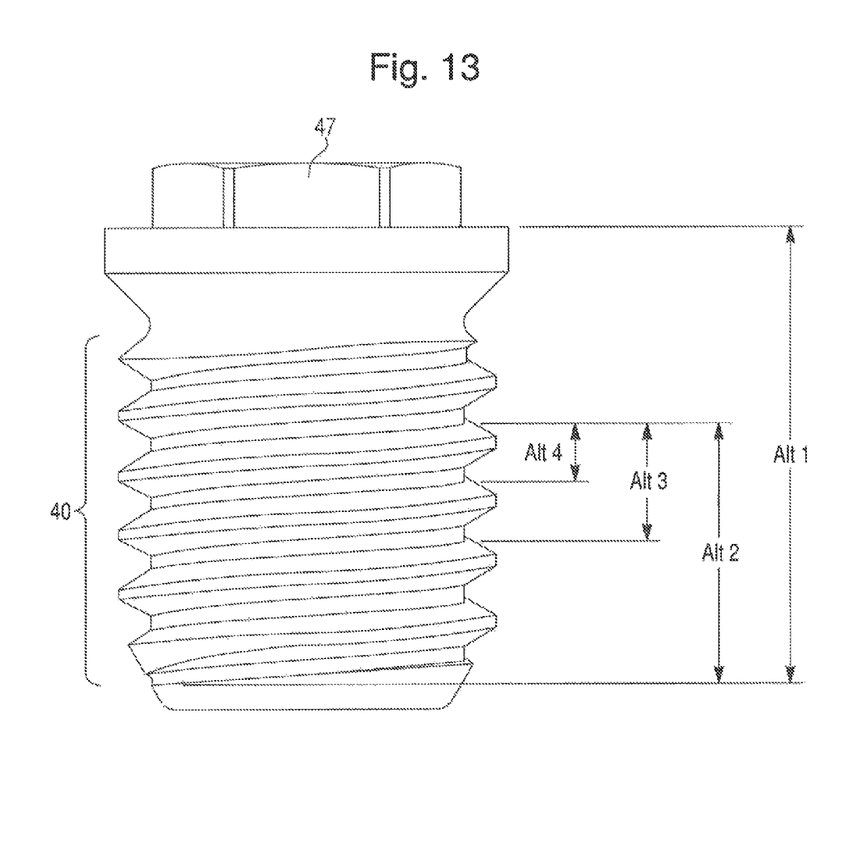
FIG. 13 is a side view of an embodiment of the implant member according to the present invention.

FIG. 13 shows a schematic dental implant of the kind shown in FIG. 10, and illustrates four different alternatives with regard to the position of said at least one surface region. According to a first alternative Alt. 1, there are one or several surface regions provided along the whole attachment means 40. According to a second alternative Alt. 2, there are one or several surface regions provided along all the turns of the thread, with the exception of the first, or the first and the second turn of the thread closest to the basis 47 of the dental implant. According to a third alternative Alt. 3, there are one or several surface regions provided along two turns of the thread adjacent to each other, preferably the third and the fourth turn of the thread in relation to the basis 47 of the dental implant. According to a fourth alternative Alt. 4, there are one or several surface regions provided along only one turn of the thread, preferably the third turn of the thread in relation to the basis 47 of the dental implant.

The position of said one or several surface regions can advantageously correspond to the deposit or deposits within each surface portion in FIG. 8 and FIG. 9, respectively.

The invention claimed is:

1. An implant member, comprising:
    means for attachment to living biological tissue of a human being or an animal, the implant having an outer surface, wherein said outer surface comprises at least one surface region, the surface of which is topographically modified, and wherein the surface region has a surface with an $S_a$ between 0.8 and 10 µm, where $S_a$ calculated by the equation:

$$S_a = \frac{1}{M*N}\sum_{j=1}^{N}\sum_{i=1}^{M}|z(x_i, y_j)|.$$

2. The implant member according to claim 1, wherein the surface region is positioned in the region of the attachment means.

3. The implant member according to claim 2, wherein the attachment means is provided with at least one thread, and that the surface region is positioned in the root of said at least one thread.

4. The implant member according to claim 3, wherein the surface region extends at least one turn of the thread.

5. The implant member according to claim 1, wherein the surface region is patterned by providing several recesses.

6. The implant member according to claim 5, wherein said recesses are provided after each other along the longitudinal extension of the root of said at least one thread.

7. The implant member according to claim 6, wherein the surface region, through said recesses, has a wave shape in a cross-section plane of the attachment means.

8. The implant member according to claim 1, wherein the outer surface of the implant member consists of titanium or titanium alloys.

9. The implant member according to claim 1, wherein $S_a$ is between 1.2 and 5 µm.

10. A method for producing an implant member, comprising:
    providing an implant member including means for attachment to living biological tissue of a human being or an animal, the implant having an outer surface, wherein said outer surface comprises at least one surface region, the surface of which is topographically modified, and wherein the surface region has a surface with an $S_a$ between 0.8 and 10 µm, where $S_a$ is calculated by the equation:

$$S_a = \frac{1}{M*N}\sum_{j=1}^{N}\sum_{i=1}^{M}|z(x_i, y_j)|;$$

and
    patterning said surface region by means of laser.

* * * * *